US006251479B1

(12) United States Patent
Groitzsch et al.

(10) Patent No.: US 6,251,479 B1
(45) Date of Patent: Jun. 26, 2001

(54) BODIES CONTAINING SUPERABSORBER POLYMERS, METHODS OF PRODUCING SUCH BODIES, AND THE USE OF SUCH BODIES

(75) Inventors: Dieter Groitzsch, Hirschberg; Gerhard Schaut, Hemsbach, both of (DE)

(73) Assignee: Firma Carl Freudenberg, Weinheim (DE)

( * ) Notice: Subject to any disclaimer, the term of this patent is extended or adjusted under 35 U.S.C. 154(b) by 0 days.

(21) Appl. No.: 09/233,845

(22) Filed: Jan. 19, 1999

(30) Foreign Application Priority Data

Jan. 19, 1998  (DE) ............................................... 198 01 680

(51) Int. Cl.⁷ ........................................................ B05D 5/04
(52) U.S. Cl. ...................... 427/244; 427/245; 427/389.9; 427/394
(58) Field of Search .................... 427/244, 336, 427/389.9, 394, 245

(56) References Cited

U.S. PATENT DOCUMENTS

| | | | |
|---|---|---|---|
| 5,149,335 | 9/1992 | Kellenberger et al. | 604/372 |
| 5,328,935 | 7/1994 | Van Phan et al. | 521/64 |
| 5,763,067 | * 6/1998 | Bruggemann et al. | 428/317.9 |
| 6,103,358 | 8/2000 | Brüggemann et al. | 428/317.9 |
| 6,136,873 | 10/2000 | Hähnle et al. | 521/62 |

FOREIGN PATENT DOCUMENTS

| | | |
|---|---|---|
| 196 07 551 | 9/1997 | (DE) . |
| 0 453 286 | 10/1991 | (EP) . |
| WO 94/22502 | 10/1994 | (WO) . |
| WO 95/31500 | 11/1995 | (WO) . |

* cited by examiner

*Primary Examiner*—Shrive Beck
*Assistant Examiner*—Kirsten A. Crockford
(74) *Attorney, Agent, or Firm*—Kenyon & Kenyon

(57) ABSTRACT

Bodies containing superabsorber polymers, having superabsorber polymers bonded together with polymer fibers, wherein at least part of the superabsorber polymers are present as a microporous open-celled foam. The bodies are used for producing diapers, sanitary napkins, tampons and other articles of personal hygiene.

9 Claims, No Drawings

BODIES CONTAINING SUPERABSORBER POLYMERS, METHODS OF PRODUCING SUCH BODIES, AND THE USE OF SUCH BODIES

BACKGROUND OF THE INVENTION

1. Field of the Invention

The present invention relates to bodies containing superabsorber polymers, methods of producing such bodies, and the use of such bodies, in particular for producing diapers, sanitary napkins, tampons and other articles of personal hygiene.

2. Description of Related Art

Absorbent structures, as are used for example in baby diapers, adult diapers and feminine hygiene, preferably contain so-called superabsorbers to increase the quantity of absorbable body fluid, make the diapers thinner and bind body fluids chemically within the developing gel body of the superabsorber. Leakage is thus prevented.

The SAP content in absorbent structures has been increased more and more over the past few years, with the following objectives: to reduce the thickness of the absorbent products, and to bind the body fluids in such a way that they are not released again even under mechanical stress (while being worn on the body, during movement, under pressure). Here the introduction of SAP in such products has proved successful because the fluid is bound to the SAP chemically, and not by capillary means. In this context, the fibers or fiber materials essentially have the function of transporting the fluid as rapidly as possible to the SAP, and the SAP itself has the function of receiving the fluid (reservoir function). It has been possible largely to avoid the problem of leakage and keep the skin dry by using special design features in the diaper, sanitary napkin, etc., primarily by backing the article with a thin non-fluid-permeable medium (a film) and further providing on the side toward the body a covering with an open structure, such as a thin, hydrophilic or hydrophilized nonwoven fabric or film with vacuum-expanded, three-dimensional perforations, and by using barrier leg cuffs and incorporating elastic elements. However, the advantage of the SAP—very high, pressure-resistant fluid uptake—is offset by the drawback of gel blocking and the associated slowing of fluid transport. Known means of enhancing gel stability, or endowing the SAP particles with a core/sheath structure in which the core is more tightly cross-linked than the sheath, result in a reduction of fluid absorption.

SAP (standing for superabsorber polymer) is known in a variety of embodiments, such as homophilic fibers composed 100% of SAP, bicomponent fibers having a core of nonabsorbent thermoplastic and a sheath of SAP, and finer and coarser powders.

SAP fibers blended with other fibers may be processed using known dry laying techniques to produce a fluid-absorbent nonwoven fabric. Although ease of processing argues in favor of such fibers made of SAP or containing an SAP component, one drawback is their relatively high price, particularly in comparison to fine and coarse powders or other particulates. An SAP staple fiber based on polyacrylic acid (or its sodium salt) costs approximately three times the price of SAP in powder form. For that reason, such fibers have not been able to achieve widespread acceptance, particularly for hygiene applications. Bicomponent fibers, in which only the sheath is made of SAP, have proved to be especially disadvantageous from the price standpoint. The sheath component constitutes only one-third to at most one-half of the total fiber mass. The absorption capacity is thus reduced accordingly and the cost of the fiber in relationship to absorbent effect is even less advantageous.

Using known dry compacting methods, such as mechanical interlacing or calendering in sheets or patterns, SAP fibers mixed with other fibers may be made into nonwoven fabrics, in which the risk of the SAP particles escaping is substantially reduced compared to SAP in other particulate forms. The SAP powder is added either by sprinkling onto a dense sheetlike body, such as tissue paper, or by dispersion within an open-pored, voluminous fiber structure. A loose deposition of fine SAP powder, or of nonfibrous SAP particles in other form, in an absorbent layer, is not advantageous. The position of the particles may change undesirably during use. In the worst case, the particles may escape from the absorbent product, if open-structured surfaces and/or open edges are present.

Numerous proposed solutions exist for fixing SAP particles to the fibers of the absorbent structures, or in other words, either within the sheetlike body or on the surface of the sheetlike body.

Diverse methods for moist pretreatment of the sheetlike body prior to the application of SAP powder, as well as dry (i.e., thermal) fixation methods, have been proposed in order to localize SAP particles on or within the absorbent article.

From European Patent A-0 719 531 it is known how to pretreat the support medium for the SAP with moisture/water. After the application or incorporation of the SAP particles, the water-soluble components of the SAP (inherent components) are activated to form a bond. After drying, the SAP particles are firmly bonded to the fibers of the absorbent layer.

In U.S. Pat. No. 3,070,095, a process is described in which SAP is sprinkled onto a tissue paper, then covered with a second tissue paper and compressed into a laminate by pressing between smooth rollers. This method, however, has the drawback that very little SAP can be applied, and the SAP is not penetrated with fibers and is thus only very weakly bonded. SAP powder escapes under the slightest mechanical stress. Moreover, such a liminate has an extreme tendency toward gel blocking, a characteristic of grave concern in hygiene applications.

WO 90/11181 and WO 91/10413 propose that fibers should be premoistened with an aqueous polymer dispersion instead of water. After drying, both the bonding forces of the synthetic polymer in the dispersion and the inherent bonding forces of the SAP particles come into play.

In all cases described thus far, the SAP particles are bonded to the fibers or incorporated into or onto the sheetlike body. But drying proves to be difficult and requires considerable outlay, because the water bound up in the SAP strongly resists re-release.

A great drawback of these SAP fixation methods is the fact that bonding is guaranteed only in the dry state. As soon as a gel body or hydrogel is formed from the SAP after the adsorption of fluid, the bonding force drops to zero or nearly zero.

European Patent A-0 720 488 describes a dry method for the fixation of SAP powder within a nonwoven fabric as the support medium for that powder. It proposes bonding fibers, either single-component (homophilic fibers) or bicomponent fibers having a higher-melting-point core and a lower-melting-point or lower-softening-point sheath. SAP is bonded to the fibers by fusion onto the bonding fibers, but in this case as well, the bonding force is almost entirely lost after the SAP is charged with fluid.

Solutions have also been proposed for giving fibers a coating of superabsorber. According to a method described in U.S. Pat. No. 4,721,647, a monomer, such as acrylic acid, methacrylic acid or vinylsulfonic acid, dissolved in water, is applied by drops to the fibers of an absorbent article, and is cross-linked there in the presence of initiators and cross-linking agents, to form a fiber coating of SAP. The concept is based on the fact that the SAP firmly envelops the fiber and is firmly bonded to the fiber even after swelling into a hydrogel-like state.

All methods described above for the application of SAP, via non-water-soluble precursors or olefin-unsaturated monomers, result in a substantial hardening in a nonwoven fabric, in comparison to the state of the fabric prior to the application of SAP, and at times cause a considerably lower application than when SAP powder is dispersed in the fabric.

SUMMARY OF THE INVENTION

The object of the present invention is to provide absorbent structures containing SAP that avoid the drawbacks of the known structures, avoid hardening in a nonwoven fabric and gel blocking during use, and retain absorbed fluid well.

The object is accomplished according to the present invention by bodies containing superabsorber polymers, having superabsorber polymers bonded together with polymer fibers, at least part of the superabsorber polymers being present as a microporous open-celled foam.

The body containing SAP according to the present invention eliminates or reduces the aforementioned drawbacks because the SAP particles have a special microporous, open-celled structure and are distributed in this structure within the absorbent product.

DETAILED DESCRIPTION OF THE INVENTION

The structure may also be called a microporous sponge structure. By particles, here we mean any kind of form for deposition on and distribution within the absorbent product. The microporous SAP may surround the fibers uniformly, constitute a pearly coating over the fibers of the absorbent product, have an entirely irregular distribution around and between the fibers, and/or be positioned at the points of intersection between fibers and there perform the function of a bonding substance for the fibers. The polymer fibers may already have adequate integrity in a prior stage of production, particularly prior to the addition of SAP, so that a further enhancement of integrity is not necessary, although it may be desired. The stage of the absorbent product prior to the application of SAP may therefore be a nonwoven fabric, which has adequate integrity for final use thanks to known nonwoven laying methods and known compacting methods.

But webs or sheets of loose unbonded fibers may also be used for SAP application. Such webs or sheets cannot be transported, or otherwise handled or processed further, without being supported. In this case the invention is configured in such a way that all, or part of the total, of the microporous foam or microporous SAP particles are solely or primarily responsible, as a bonding agent, for the integrity of the absorbent product.

The foam structure of the SAP particles is open-celled, or predominantly open-celled. By this is meant the fact that up to 100% of the pores contained within the SAP connect with one another. Because of the penetrating microchannels within the SAP particles in the absorbent product, the fluid is transported more rapidly into the core of the product than with conventional compact SAP masses. Because of the extremely hydrophilic nature of the microporous SAP structure, aqueous media are very rapidly transported into the core of the particle, despite the small pore size. The pore size is in the range from 0.2 to 100 $\mu$m, and preferably from 0.5 to 50 $\mu$m.

Within and on the SAP, wetting agents or other surfactants may be applied or integrated, further reducing the interfacial tension between the SAP polymer and water. This accelerates fluid transport both in the micro range—i.e., within the SAP—and in the macro range—i.e., within the volume of the absorbent product as a whole.

The absorbent body according to the present invention may be used directly, or may be a component of an absorbent product having a multilayer structure. Such multilayer products are used, for example, in baby diapers, adult diapers and sanitary napkins. It is known how to place an absorbent core between a top sheet and a non-fluid-permeable backing film. Between the core and the top sheet may be interposed a further layer which spontaneously absorbs body fluid and transmits it to the core, after a time lag, for final storage, primarily within the SAP and to some extent in the intercapillary spaces between the fibers. This intermediate layer can largely prevent gel blocking.

The present invention also relates to such a multilayer body containing, in the following order:

1) a fluid-permeable top sheet
2) a sheetlike layer of a body according to the present invention, and
3) a non-fluid-permeable layer.

The body containing superabsorber polymers may assume any desired shape. Preferably, for uses in diapers, sanitary napkins or panty liners, it is in a sheetlike shape. For use in the form of tampons, it may also, for example, be in a cylindrical or similar shape.

In the body according to the present invention, at least part of the SAP is present as a microporous, open-celled foam. Together with this, other non-foam SAP particles may also be present. However, preferably all the SAP, or essentially all the SAP, is present as a microporous, open-celled foam.

The distribution of the spongy, microporous SAP within the absorbent body may extend throughout the cross-section. But its distribution may also be limited to only part of the cross-section, so that one side is entirely free from SAP. It may be more concentrated on one side than on the other side, so that a distribution gradient exists perpendicular to the surface, from one surface to the other. The side with the higher open-celled SAP particle density will then preferably be turned toward the core or the non-fluid-permeable film backing.

In a further embodiment of the present invention, entirely poreless SAP particles may be embedded in and/or deposited on, as indicated above, the SAP having a microporous foam structure, or be distributed in any other manner within or on the microporous structure. This may be an advantage when it is less important to cause the SAP to swell quickly, i.e., to have greatly accelerated fluid uptake, and instead for reasons of application technology it is opportune to increase the quantity of superabsorbent material per unit volume of the absorbent product as a whole.

The product according to the present invention is characterized not only by a very greatly accelerated fluid uptake in the micro range of the SAP, but additionally by an extreme softness, conformability and deformability. These characteristics are especially prized in absorbent products such as diapers in particular, so as to prevent leakage after the emission of the body fluid. With such products, conformation to body shapes, in combination with elastic, is much better than in the case of stiffer, less pliant and more rigidly bonded products.

The SAP may in principle be composed of polymers such as absorb at least 20 times their own dry weight in fluid, while forming no hydrogel. The superabsorber polymer is preferably selected from among hydrophobically modified hydrocarbon polymers, poly(vinyl alcohol-co-vinyl acetate), poly(meth)acrylic acid, cyanoethylated or partially formylated poly(vinyl alcohol), poly-N-vinyl-2-oxazolidone, polypeptides, (meth)acrylate copolymers or N-alkyl(meth)acrylamide derivatives. Such polymers include salts of polyacrylic acid or copolymers contained by the copolymerization of acrylic acid and such comonomers as maleic acid, itaconic acid, acrylamide, 2-methylpropanesulfonic acid, 2-methacrylic ethanesulfonic acid, 2-hydroxyethyl methacrylate or styrenesulfonic acid, at a copolymerization ratio that does not adversely affect the characteristics of the SAP.

The method described below for producing the absorbent product requires the use of water-soluble polymer or pre-polymer substances having reactive, cross-linkable groups. Typical functional groups that may easily be brought into reaction with suitable cross-linking agents are hydroxyl, amino and carboxyl groups. The water-soluble polymers lose their water solubility through cross-linkage, and are converted to a non-water-soluble but swellable state.

Examples of such water-soluble polymers are hydroxyalkylated starches, hydroxyalkylated guar and hydroxyalkylated dextran, copolymers of vinyl alcohol and vinyl acetate, polymethacrylic acid, acrylate or methacrylate copolymers such as poly(hydroxypropyl acrylate-co-acrylamide), poly(hydroxyethyl acrylate-co-diacetone acrylamide) and poly(hydroxypropyl acrylate-co-hydroxyethyl acrylate).

The SAP is preferably selected from among hydroxypropyl dextran, hydroxypropyl guar, hydroxypropyl starch, hydroxypropyl cellulose, hydroxyethyl cellulose, methylcellulose, hydroxypropyl methylcellulose, and ethylhydroxyethyl cellulose.

Examples of suitable polypeptides are poly(L-proline) and poly(valine-proline-lycine-X-glycine) where X=any desired amino acid.

Hydroxypropyl cellulose or hydroxyethyl cellulose, especially hydroxypropyl cellulose, is used by particular preference. In the finished body containing SAP, the SAPs are cross-linked. Examples of suitable cross-linking agents are acetaldehyde, formaldehyde, glutaraldehyde, diglycidyl ether, divinyl sulfone, diisocyanate, dimethyl urea, epichlorohydrin, oxalic acid, phosphoryl chloride, trimetaphosphate, trimethylol melamine, polyacrolein-like compounds. Formaldehyde, glutaraldehyde, divinyl sulfone and epichlorohydrin are preferred.

According to the present invention, all suitable polymer fibers may be used as polymer fibers. Examples of suitable fibers are polyethylene fibers, polypropylene fibers, polyethylene terephthalate fibers and other fibers that are usually used for producing diapers and similar products.

The bodies containing SAP according to the present invention are produced by:
a) Mixing a cross-linkable SAP with a solvent to form an SAP solution which can be separated into phases, and impregnating the polymer fibers with this solution,
b) Inducing a phase separation of the SAP solution into a phase containing fibers and enriched with polymer, and a phase impoverished in polymer,
c) During the phase separation, cross-linking the SAP in the polymer-enriched phase containing fibers, to form a microporous, open-celled foam on the fibers, and
d) Drying the resulting body containing SAP while maintaining the microporous, open-celled structure in the SAP.

Such a method for producing SAP foams that are not in contact with polymer fibers is described, for example, in WO 95/31500. The method described in that publication is preferably followed to produce the bodies according to the present invention.

The induction of phase separation is preferably accomplished by heating, if applicable in a water-vapor atmosphere, to a temperature in the range up to 98° C., or by the addition of volatile nonsolvents for the SAP.

The method is based on causing a solution of a cross-linkable polymer to undergo phase separation by initiating cross-linking, and if applicable by adding agents to accelerate phase separation. One phase becomes impoverished in polymer, and the other becomes enriched with polymer. In the polymer-enriched phase, cross-linking is continued until a microporous foam has formed through coagulation. Finally drying is performed. The process up to the stage of pore formation preferably takes place in a previously produced, hermetically sealed mold. The wet sponge is removed from the mold for drying.

The preferred process according to the present invention is based upon slowly heating to 98° C., in a water-vapor atmosphere, a loose fiber web or already previously bonded nonwoven fabric, after the application of a cross-linkable, aqueous polymer solution mixed with a cross-linking agent, the cross-linking and the associated precipitation of the microporous structure having already been initiated during the heating period and being completed, likewise in a water-vapor atmosphere, after the final temperature is reached. The separation of the SAP here may be accelerated by the addition of electrolytes or other known nonsolvents for the polymer dissolved in water. After the cross-linked product has been entirely precipitated, drying is performed. To accelerate drying, a solvent exchange, known per se, may previously be performed, such that water in the micropores is initially displaced by a first water-soluble solvent like ethanol, which in turn is displaced by a second solvent, such as heptane, that has a very low boiling point compared to the first solvent.

The further process parameters may be found in WO 95/31500. The heating of the polymer solution preferably proceeds at a temperature above the lower separation temperature. Precise information about the lower separation temperature, as well as the concentrations of polymer and cross-linking agent in the solution, may be found in the above publication. Information about the employed reaction times and temperature curves may also be obtained from WO 95/31500.

The bodies or multilayer bodies containing SAP, according to the present invention, are preferably used for producing diapers, sanitary napkins, tampons, or other articles of personal hygiene.

What is claimed is:
1. A method for manufacturing a fabric containing superabsorbers, comprising the steps of
a) mixing a cross-linkable superabsorber polymer with a solvent to form a superabsorber polymer solution which can be separated into phases, and impregnating the polymer fibers with this solution,
b) inducing a phase separation of the superabsorber polymer solution into a phase containing fibers and enriched with polymer, and a phase depleted of polymer, c) during the phase separation, cross-linking the superabsorber polymer in the polymer-enriched phase containing fibers, to form a microporous, open-celled foam on the fibers, and d) drying the resulting body containing superabsorber polymer while maintaining the microporous, open-celled structure in the superabsorber polymer.

2. The method as recited in claim 1, wherein the induction of phase separation is accomplished by heating to a temperature in the range of up to 98° C., or by the addition of liquid nonsolvents for the superabsorber polymer.

3. The method as recited in claim 2, wherein heating is carried out in a water-vapor atmosphere.

4. A method for manufacturing a fabric containing superabsorbers, comprising the steps of:

a) mixing a cross-linkable superabsorber polymer with a solvent to form a superabsorber polymer solution which is separated into phases, and impregnating polymer fibers with this solution, b) inducing a phase separation of the superabsorber polymer solution into a phase containing fibers and enriched with polymer, and a phase depleted of polymer, c) during the phase separation, cross-linking the superabsorber polymer in the polymer-enriched phase containing fibers, to form a microporous, open-celled foam on the fibers, and d) drying the resulting fabric containing superabsorber polymer while maintaining the microporous, open-celled structure in the superabsorber polymer.

5. The method as recited in claim 4, wherein the induction of phase separation is accomplished by heating to a temperature in a range of up to 98° C.

6. The method as recited in claim 4, wherein the polymer fibers are used as a pre-bound non-woven fabric.

7. The method as recited in claim 4, wherein the polymer fibers are employed as a loose fleece.

8. The method as recited in claim 4, wherein the step of inducing phase separation is accomplished by heating.

9. The method as recited in claim 8, wherein the heating is conducted in a water vapor atmosphere or with addition of liquid nonsolvents for the superabsorber polymer.

\* \* \* \* \*